United States Patent
Dantas De Almeida et al.

(10) Patent No.: US 10,988,771 B2
(45) Date of Patent: Apr. 27, 2021

(54) **ENDOSPERM-SPECIFIC PROMOTER FROM THE LIPID TRANSFER PROTEIN 1 GENE OF *COFFEA ARABICA***

(71) Applicant: EMPRESA BRASILEIRA DE PESQUISA AGROPECUÁRIA—EMBRAPA, Brasilia (BR)

(72) Inventors: Juliana Dantas De Almeida, Brasilia (BR); Leila Maria Gomes Barros, Brasilia (BR); Mauro Carneiro, Brasilia (BR); Alan Carvalho Andrade, Brasilia (BR); Felipe Rodrigues Da Silva, Campinas (BR); Luiz Filipe Protasio Pereira, Londrina (BR); Michelle Guitton Cotta, Brasilia (BR); Mirian Therezinha Souza Da Eira, Brasilia (BR)

(73) Assignee: EMPRESS BRASILEIRA DE PESQUISA AGROPECUÁRIA—EMBRAPA, Brasiília (BR)

( * ) Notice: Subject to any disclaimer, the term of this patent is extended or adjusted under 35 U.S.C. 154(b) by 330 days.

(21) Appl. No.: 14/391,066

(22) PCT Filed: Apr. 9, 2013

(86) PCT No.: PCT/BR2013/000110
§ 371 (c)(1),
(2) Date: Mar. 23, 2015

(87) PCT Pub. No.: WO2013/152408
PCT Pub. Date: Oct. 17, 2013

(65) Prior Publication Data
US 2015/0197762 A1    Jul. 16, 2015

(30) Foreign Application Priority Data
Apr. 9, 2012  (BR) .......................... 102012008162-8

(51) Int. Cl.
*C12N 15/82*    (2006.01)
(52) U.S. Cl.
CPC ................ *C12N 15/8234* (2013.01)
(58) Field of Classification Search
None
See application file for complete search history.

(56) References Cited

U.S. PATENT DOCUMENTS 6,031,152 A * 2/2000 Olsen .................. C07K 14/415
                                                 435/320.1
6,441,273 B1   8/2002 Aldwinckle et al.

OTHER PUBLICATIONS

Thoma et al. Tissue-specific expression of a gene encoding a cell wall-localized lipid transfer protein from *Arabidopsis*. (1994) Plant Physiology vol. 105; pp. 35-45.*
Potenza et al. Invited Review: targeting transgene expression in research, agricultural, and environmental applications: promoters used in plant transformation. (2004) In Vitro Cell. Dev. Biol.; vol. 40; pp. 1-22.*
Benfey et al. The cauliflower mosaic virus 35S promoter: combinatorial regulation of transcription in plants. (1990) Science; vol. 250; pp. 959-966 (Year: 1990).*
Kim et al. A 20 nucleotide upstream element is essential for the nopaline synthase (nos) promoter activity. (1994) Plant Molecular Biology; vol. 24; pp. 105-117 (Year: 1994).*
Donald et al. Mutation of either G box or I box sequences profoundly affects expression from the *Arabidopsis* rbcS-1A promoter. (1990) The EMBO Journal; vol. 9; pp. 1717-1726 (Year: 1990).*
Exogenous; definition (2020) downloaded from the internet on Mar. 11, 2020; link to website in office action on p. 7. (Year: 2020).*
International Preliminary Report on Patentability, dated Oct. 14, 2014, issued by the International Searching Authority in counterpart Application No. PCT/BR2013/000110.
Cotta et al., "Isolation and Characterization of Fruit Specific Promoter for CALTP1 Gene in *Coffea Arabica*", VII Simpósio de Pesquisa dos Cafés do Brasil, Araxá-MG (2011).
Kalla et al., "The promoter of the barley aleurone specific gene encoding a putative 7-kDa lipid transfer protein confers aleurone cell-specific expression in transgenic rice", Plant J., 6:849-860 (1994).
Boutrot et al., "Wheat non-specific lipid transfer protein genes display a complex pattern of expression in developing seeds", Biochimica et Biophysica Acta, 1730:114-125 ( (2005).
Boutrot et al., "The *Triticum aestivum* non-specific lipid transfer protein (TaLtp) gene family: comparative promoter activity of six TaLtp genes in transgenic rice", Planta, 225:843-862 (2007).

* cited by examiner

*Primary Examiner* — Cathy Kingdon Worley
(74) *Attorney, Agent, or Firm* — Sughrue Mion, PLLC

(57) ABSTRACT

The present disclosure relates to a promoter sequence from the lipid transfer protein 1 gene of *Coffea arabica*. The present disclosure further describes DNA constructs that contain the promoter, as well as methods of producing transgenic plants, plant cells or protoplasts, using such constructs.

16 Claims, 5 Drawing Sheets

Specification includes a Sequence Listing.

ENDOSPERM-SPECIFIC PROMOTER FROM THE LIPID TRANSFER PROTEIN 1 GENE OF *COFFEA ARABICA*

FIELD OF THE INVENTION

The present invention relates to the field of biotechnology. More specifically, the invention relates to a specific promoter for the expression of genes of interest in fruit endosperm. The invention further describes DNA constructs that contain the promoter of the invention operatively linked to a heterologous and/or endogenous gene. Besides, the invention relates to the use of these constructs as expression vectors, recombinant vectors, plants, plant cells or transgenic protoplasts. The invention further describes a method using such constructs containing the promoter of the invention for the production of plants, plant cells or transgenic protoplasts. Thus, the expression of the transgene only in the part of interest enables the accumulation of the exogenous transcript only in the fruit, favoring the implementation of strategies armed at increasing the aggregated value, the generation of cultivars more adapted to environmental stress, pathogens and pests, agricultural defensives, in addition to plants with a high nutritional value and a high therapeutic value. In addition to these advantages, the present invention is a new alternative to the systems of expression in plant organism and may be used for generating novel cultivars and improvement programs. The present invention aims to increase the economic, social, and environment and biosafety benefits associated with transgenic transformation.

BACKGROUND OF THE INVENTION

In the last three decades, agriculture has been benefited by biotechnology, which associated the recombinant DNA technology, the culture of plant tissues and the classic improvement methods for generating plants that are more resistant to herbicides (Aragão, F. J. L., Vianna, G. R., Albino, M. M. C. & Rech, E. L. 2002 Transgenic Dry Bean Tolerant to the Herbicide Glufosinate Ammonium. Crop Science, v. 42, n. 4, p. 1298-1302), a insetos-praga (Lilley C. J., Wang D., Atkinson H. J. & Urwin P. E. 2010 Effective delivery of a nematode-repellent peptide using. Plant Biotechnology Journal, pp. 1-11 doi: 10.1111/j.1467-7652.2010.00542.x, a root-cap-specific promoter) and tolerant do drought (Quan R, Hu S, Zhang Z, Zhang H, Zhang Z, Huang R. Overexpression of an ERF transcription factor TSRF1 improves rice drought tolerance. Plant Biotechnol J. 2010 May 1; 8(4):476-88), besides plants with a high nutritional value (Aluru, M., Xu, Y., Guo, R., Wang, Z., Li, S., White, W., Wang, K. & Rodermel, S. 2008 Generation of transgenic maize with enhanced provitamin A content. J. Exp. Bot., v. 59, n. 3, p. 3551-3562) and a high therapeutic value (Marcondes, J. & Hansen, E. 2008 Transgenic lettuce seedlings carrying hepatitis B virus antigen HBsAg. Braz. J. Infect. Dis., v. 12, n. 6, p. 469-471). Taken together, these characteristics result in an increase in the production, economic gains, improvement of the quality of life of the population and preservation of the environment. By means of the transgenic technique, it is possible to introduce genes of interest regardless of interspecific barriers.

In spite of the economic, social and environmental benefits associated with genetic transformation, this technology has become the object of concern on the part of consumers and environmentalists due to biosafety issues.

Data from the literature show an evolution in the application of genetic transformation according to the appearance of various generations of transgenics. The first and second generation of transgenic plants used constitutive promoters such as the promoter of the virus of the cauliflower mosaic (CaMV 35S) (Odell, J. T., Nagy, F. & Chua, N-H. 1985 Identification of DNA sequences required for the activity of the cauliflower mosaic virus 35S promoter. Nature, v. 313, p. 810-812), gene promoters found in the T-DNA of *Agrobacterium tumefaciens*, as for example the promoter of the gene of enzyme nopaline synthase (Bevan, M. W., Barnes, W. M. & Chilton, M. D. 1983 Structure and transcription of the nopaline synthase gene region of T-DNA. Nucleic Acids Research, v. 11, n. 2, p. 369-385), and promoters of genes that encode proteins that are highly preserved and involved in vital processes of virtually all the organisms such as ubiquitin (Toki S., Takamatsu S., Nojiri C., Ooba S., Anzai H., Iwata M., Christensen A. H., Quail P. H. & Uchimiya H. 1992 Expression of a Maize Ubiquitin Gene Promoter-bar Chimeric Gene in Transgenic Rice Plants. Plant Physiol. November; 100(3):1503-7), and actin (An Y. Q., McDowell J. M., Huang S., McKinney E. C., Chambliss S. & Meagher R. B. 1996 Strong, constitutive expression of the *Arabidopsis* ACT2/ACT8 actin subclass in vegetative tissues. Plant J. July, 10(1):107-21). However, the third generation of transgenic plants is characterized, among other aspects, by the use of tissue-specific promoters such as epidermal-cell-specific promoters (Hooker T. S., Millar A. A. & Kunst L. 2002. Significance of the expression of the CER6 condensing enzyme for cuticular wax production in *Arabidopsis*. Plant Physiol. August; 129(4):1568-80), of phloem (Okumoto S., Koch W., Tegeder M., Fischer W. N., Biehl A., Leister D., Stierhof Y. D. & Frommer W. B. 2004. Root phloem-specific expression of the plasma membrane amino acid proton co-transporter AAP3. J Exp Bot. October; 55(406):2155-68), of pollen (Wakeley P R, Rogers H J, Rozycka M, Greenland A J, Hussey P J. A maize pectin methylesterase-like gene, ZmC5, specifically expressed in pollen. Plant Mol Biol. 1998 May; 37(1):187-92) or biotic stress-induced promoters (Himmelbach A., Liu L., Zierold U., Altschmied L., Maucher H., Beier F., Müller D., Hensel G., Heise A., Schützendübel A., Kumlehn J. & Schweizer P. 2010. Promoters of the barley germin-like GER4 gene cluster enable strong transgene expression in response to pathogen attack. Plant Cell. 2010. March; 22(3):937-52. Epub March 19), abiotic stress-inducible promoters (Rai M., He C. & Wu R. 2009. Comparative functional analysis of three abiotic stress-inducible promoters in transgenic rice. Transgenic Res. October; 18(5):787-99) and chemical ones (Tomsett, A. Tregova, A. Garoosi and M. Caddick, Ethanol-inducible gene expression: first step towards a new green revolution?, Trends Plant Sci. 9 (2004), pp. 159-161) to drive expression of the punctual transgene and only when necessary.

Obtaining and making available promoters capable of limiting the gene expression in time and/or space may be one of the ways to balance the benefits of transgeny and its restriction.

A promoter is a set of transcription control modules, organized around the enzyme initiation of the enzyme polymerase II (Potenza, C.; Aleman, L. & Sengupta-Gopalan, C. 2004. Targeting transgene expression in research, agricultural, and environmental applications: Promoters used in plant transformation. In Vitro Cellular Development Biological-Plant v. 40, p. 1-22), which contain specific sequences recognized by proteins involved in the transcription. Different classes of promoters have been described in the literature, based on the expression profile thereof. Among them is that of constitutive promoters, which are active in all the tissues and in all the phases of development of the organism, as for instance, CaMV35S (Odell, J. T., Nagy, F. & Chua, N-H. 1985. Identification of DNA sequences required for the activity of the cauliflower mosaic virus 35S promoter. Nature, v. 313, p. 810-812). On the other hand, tissue/organ-specific promoters drive the expression of its related gene only in its tissue/organ-target like in the fruit (Atkinson R. G., Bolitho K. M., Wright M. A., Iturriagagoitia-Bueno T., Reid S. J. & Ross G. S. 1998 Apple ACC-oxidase and polygalacturonase: ripening-specific gene expression and promoter analysis in transgenic tomato. Plant Mol Biol. October; 38(3):449-60), in grain-seed (Paine J. A., Shipton C. A., Chaggar S., Howells R. M., Kennedy M. J., Vernon G., Wright S. Y., Hinchliffe E., Adams J. L., Silverstone A. L. & Drake R. 2005. Improving the nutritional value of Golden Rice through increased pro-vitamin A content. Nat Biotechnol. April; 23(4):482-7), in root/tubercles (Visser R. G., Stolte A. & Jacobsen E. 1991. Expression of a chimeric granule-bound starch synthase-GUS gene in transgenic potato plants. Plant Mol Biol. October; 17(4): 691-9), in flowers (Annadana S., Beekwilder M. J., Kuipers G., Visser P. B., Outchkourov N., Pereira A., Udayakumar M., De Jong J. & Jongsma M. A. 2002. Cloning of the chrysanthemum UEP1 promoter and comparative expression in florets and leaves of *Dendranthema grandiflora*. Transgenic Res. August; 11(4):437-45) and leaves (Nomura M., Katayama K., Nishimura A., Ishida Y, Ohta S., Komari T., Miyao-Tokutomi M., Tajima S. & Matsuoka M. 2000. The promoter of rbcS in a C3 plant (rice) directs organ-specific, light-dependent expression in a C4 plant (maize), but does not confer bundle sheath cell-specific expression. Plant Mol Biol. September; 44(1):99-106). There are still the responsive or inducible promoters, which are activated by means of a determined situation, in response to biotic, abiotic or chemical stresses. Promoters isolated from a given organism may be used to regulate a gene of another organism by means of chimeric genic constructs.

There are numberless tissue-specific promoters described for plants, as is the case of the specific expression in seed (WO8903887), tubercle (as mentioned in patent application US20030175783, Keil et al., 1989 EMBO J. 8: 1323:1330), leaves (as mentioned in patent application US20030175783, Hudspeth et al., 1989 Plant Mol Biol 12:579-589), stem (as mentioned in patent application US20030175783, Keller et al., 1988 EMBO J. 7: 3625-3633), vascular tissues (as mentioned in patent application US20030175783, Peleman et al., 1989 Gene 84: 359-369 and Schmülling et al. (1989) Plant Cell 1, 665-670), root (US20060143735 and as mentioned in patent application US20030175783, Keller et al., 1989 Genes Devel. 3:1639-1646), stamens (WO8910396, WO9213956), dehiscence-zone-specific promoters (WO9713865), meristem (Ito et al. (1994) Plant Molecular Biology, 24, 863 a 878) and fruit (Edwards and Coruzzi (1990) Annu. Rev. Genet. 24, 275 a 303 and U.S. Pat. No. 5,753,475, in the latter document the sequence presented has specific action on the fruit pericarp).

In the present invention, we present a promoter isolated from coffee-plant (*Coffea* ssp), specific of the fruit endosperm. The endosperm is the consumed part of the grain, of great economic interest, and the possibility of expressing a protein of interest specifically in the endosperm is useful in the introduction of characteristics related to the nutritional quality, organoleptic characteristics, and advantages in the post-harvest phase. At present, the promoters used in obtaining commercial transgenics are often constitutive and drive the expression of the transgene in all the tissues of the plant and in all the phases of development. This characteristic entails energetic wear in the plant, since there is metabolic waste in the production of a protein in amounts and at places where it is unnecessary, and may lead to decrease in productivity. Besides, it is desirable, from the commercial point of view, to aggregate value to economically important crops, as is the case of golden rice, which is rich in β-caroten (Beyer P. Golden Rice and 'Golden' crops for human nutrition. 2010. May 15. N Biotechnol. [Epub ahead of print]. sciencedirect.com/science?_ob=ArticleURL&_udi=B8JG4-5033Y3B2&_user=7430124&_coverDate=05%2F15%2F2010&_rdoc=1&_fmt=high&_orig=search&_sort=d&_docanchor=&view=c&_acct=C000012878&_version=1&_urlVersion=0&_userid=7430124&md5=a9c6d210db86be4e6946f0f1f69766c0).

Another important aspect is the biosafety tests are made easier, since the expression of the gene is restricted to a single organ.

Increasingly frequent use of transgeny as a means to solve problems of economically important crops occurs because transgeny enables the incorporation of desirable characteristics in a targeted manner, regardless of barriers between species.

Most transgenic plants launched on the market so far make use of constitutive promoters, the product of which is expressed in all the tissues of the organism. Another limiting factor is the technological dependence, since the use of the promoters available at present are protected by patents. The invention proposed herein can be further viewed as an alternative to existing promoter regions, chiefly in cultivars and improvement programs.

The present agronomic scenario is subject to impacts promoted by weather changes, which cause serious unbalances in the environment and in agriculture, as well as to the population increase, which is a factor that generates environmental unbalance due to the demand for space to increase the agricultural production. In order to mitigate these impacts, it is necessary to handle natural resources like water and space in a sustainable way, as well as adversities like drought, pests and pathogens. Thus, plants that are more adequate to this scenario need to be developed, and transgeny is a tool that accelerates the obtainment of these cultivars.

Document PI0209551-3 presents an invention that relates to a nucleotide sequence derived from coffee-plant leaves, which can be used as a promoter for a gene-inducible expression in plants. Particularly, said invention belongs to a nucleotide sequence embracing the promoter and the region encoding an rbcS gene. In a different way, the invention proposed in the present document relates to a fruit-specific promoter and, in addition consists of an alternative to transgeny processes, particularly in plant organisms.

Documents WO0151637 and WO0302939 relate to promoters isolated from *Fragaria vesca*—strawberry, which direct selectively the expression of DNA sequences placed under control thereof in plant fruits. When compared to the present invention, it is observed that the promotor sequences described in the above-cited patents were isolated from *Fragaria vesca*—strawberry. The proposal disclosed in the present document has, as an advantage, its use for generating cultivars and/or improvement programs in various plant organisms, including those belonging to the genus *Coffea* ssp, since the isolate was obtained from the same genus. Besides, the proposed promoter presents an alternative to the creation of plant organisms expressing transgenes.

Patent KR100797644, in turn, relates to a fruit-specific expression promoter derived from *Citrus unshiu*—a citrus fruit of Japanese origin. The promoter is provided to induce the expression in the late maturation period in fruits, efficiently express a foreign gene in fruits and control its expression, so that transgenic plants are efficiently produced. The advantage in using the invention proposed by our group arises particularly in the cultivars of the genus *Coffea* ssp or even in programs for improving this genus, since this is a regulatory region present in the genus itself. It also presents an alternative to the creation of plant organisms expressing transgenes, as mentioned above.

Document WO2010093175 presents a specific expression. Promoter of the gene HR7, while document WO2010012848 relates to a sequence called FSP1, located in 5' region of the DNA of the gene Sn1, both derived from *Solanum lycopersicum*—tomato. According to this document, a gene introduced from a transformed plant can be specifically expressed in tissues of flowers and fruits, as compared to that used conventionally, as for example, the Cauliflower mosaic virus—CaMV 35S promoter. In spite of being a specific promoter and it may be used for expression in fruits, this promoter presents, as disadvantage to the promoter claimed herein, the impossibility of being used as a native promoter of the genus *Coffea* ssp and/or programs of improving this genus.

The inventions disclosed in documents CN1298021 and WO2005026366 refer to sequences for directing the expression of a gene of interest in the endosperm. These sequences are derived from the 5"controlling sequences of the waxy gene and of the glutelin gene GluD-1 of rice, respectively, thus having the same disadvantages cited in the preceding paragraph with regard to the genus *Coffea* ssp.

The invention presented in document US2007169226 relates to methods and reactants for the gene expression regulated in time and/or space, especially in plant seeds and related female reproductive tissues. However, the compositions comprise novel nucleotide sequences for a promoter that is known to control the expression in seeds, of the gene known as eep1, and not of fruits specifically. Besides the fact that this sequence is not specific for *Coffea* ssp.

Very similar the document of the preceding item, document WO2008040061 discloses an isolated nucleic acid sequence comprising a nucleotide sequence that corresponds to an active promoter region of a DNA sequence. However, the isolated nucleic acid sequence is derived from a cereal grain and brings the same disadvantages referring to the use of the promoter in the genus *Coffea* ssp and in the programs of improving said genus.

Still similarly, documents US2009089897 and US2010037347 provide compositions and methods for regulating the expression of nucleotide sequences in plant, wherein the new compositions are nucleotide sequences for tissue promoters, but isolated from sorgo.

Document WO2010118477, in turn, provides compositions comprising promoter sequences operable in plants, isolated from *Triticum aestivum*—wheat, and variants thereof, which impart selective/specific expression. Of specific genes, especially in the endosperm, thus being diferente and not having the advantages of the sequences proposed herein with regard to the genus *Coffea* ssp.

U.S. Pat. No. 7,071,378 and patent application WO2005026366 disclose isolated promoter nucleotide sequences, respectively of *Zea mays*—maize and *Hordeum vulgare*—barley, which enable the expression of encoding sequences, where they can be attached, which are specific for the endosperm region.

In the face of the above, the present invention relates to an endosperm-specific promoter sequence for the expression of a gene of interest only in the fruit. In addition to presenting advantages such as the expression direct only at the fruits endosperm, and upon being used in cultivars of *Coffea* ssp and programs of improvement of the same genus, the invention further brings a new alternative to expression systems in plants.

SUMMARY OF THE INVENTION

The invention relates to a novel promoter for gene-specific expression in fruit endosperm. Thus, the expression of the transgene only in the part of interest enables accumulation of the exogenous transcript only in the fruit, favoring the implementation of strategies that arm at the increase in the aggregated value, the generation of cultivars more adapted to the environmental stress, pathogens and pests, agricultural defensives, besides plant organisms with a high nutritional value and a high therapeutic value. In addition to these advantages, the present invention is a new alternative to expression systems in plant organisms and may be used for generating new cultivars and improvement programs. The invention has the objective of increasing the economic, social and environment and biosafety benefits associated with genetic transformation.

In a first embodiment, the present invention provides a polynucleotide sequence that is substantially similar to the SEQ ID NO: 1; reverse sequence of SEQ ID NO: 1; probes and primers corresponding to the SEQ ID NO: 1.

In another aspect, the present invention provides chimeric genes comprising the polynucleotide of the present invention, either alone or in combination with one or more known polynucleotides, together with cells and organisms comprising these chimeric genes.

In a related aspect, the present invention provides recombinant vectors comprising, in the 5'-3' direction, a promoter polynucleotide sequence of the present invention, a transcribable polynucleotide, and a gene termination sequence. The transcribable polynucleotide comprising an open reading frame of a polynucleotide that encodes a polypeptide of interest, or comprising a non-coding region, or a non-translated region, of a polynucleotide of interest. The open reading frame may be oriented in a "sense" or "antisense" direction. Preferably, the gene termination sequence is functional in a host plant. More preferably, the gene termination sequence is that of the gene of interest, or it may be any other of those described in the prior art (see Benjamin Lewin, Genes VIII, CHAPTER 9), as for example the terminator of the nopaline synthase of *A. tumefaciens*. The recombinant vectors may further include a marker for identification of transformed cells.

In another aspect, the transgenic plant cells comprising the recombinant vector of the present invention are provided, together with organisms, like plants, comprising these transgenic cells, and fruits, seeds and other products, derivatives, or progeny of these plants. The propagules of the transgenic plants obtained by the present invention are also included herein.

In another aspect, the present invention provides a method for modifying the expression of genes in an organism, like a plant, including the stable incorporation into the genome of the organism containing the recombinant vector of the present invention.

In another aspect, the present invention provides a method for producing a transformed organism, like a plant, having the modified expression of a polypeptide. The method comprising transforming a plant cell with the recombinant vector of the present invention to provide a transgenic cell under conditions that lead to the regeneration and growth of the mature plant.

In a further aspect, the present invention provides a method for identifying a gene responsible for a function of desired phenotype. The method comprising: (1) transforming a plant cell containing a recombinant vector comprising a promoter polynucleotide sequence of the present invention, optionally linked to a polynucleotide to be tested; (2) cultivating the plant cell under conditions that lead to the regeneration and growth of the mature plant, in order to provide a transgenic plant; and (3) comparing the phenotype of the transgenic plant with the phenotype of non-transformed plants, or of a wild type.

The above-mentioned and additional aspects of the present invention and how to obtain them will become evident, and the invention will be better understood by reference in the "Detailed Description of the Invention".

DESCRIPTION OF THE INVENTION

Figure 1:
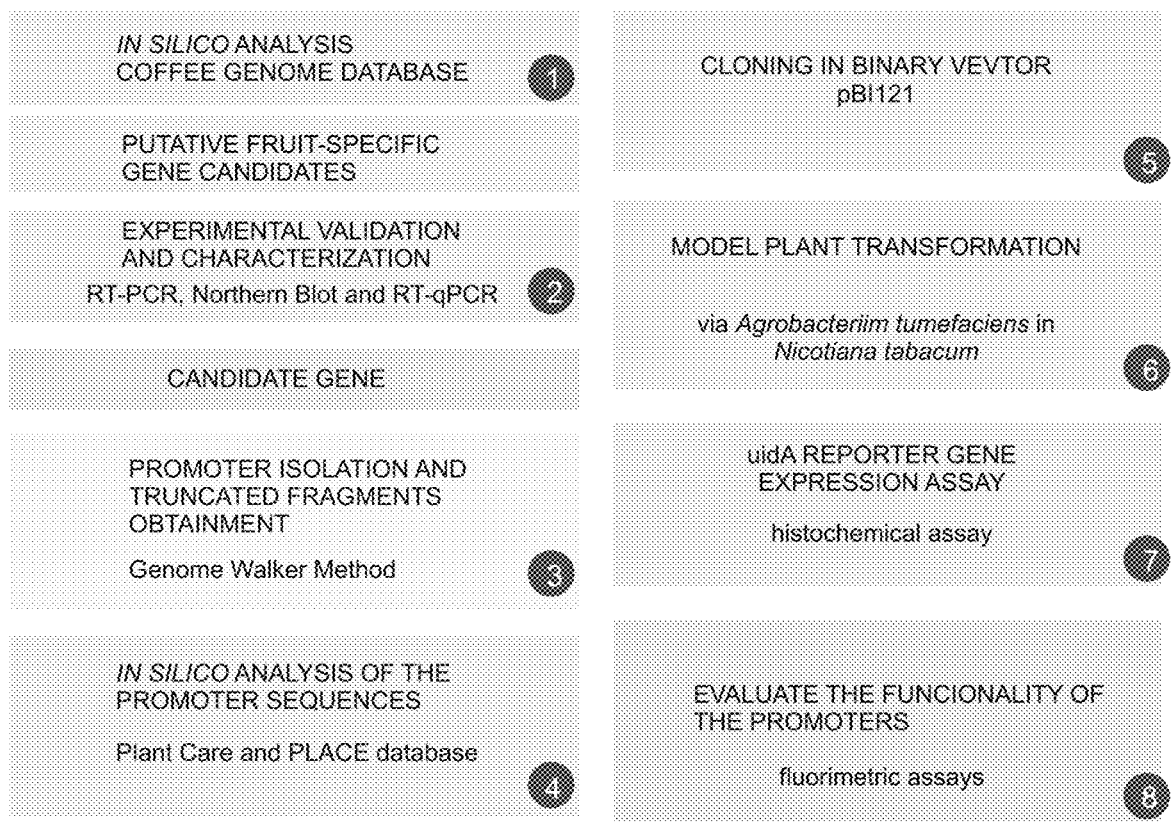
FIG. 1—a flowchart presenting the steps involved in the development of the endosperm-specific promoter.

The present invention relates to an endosperm-specific promoter for the expression of a gene of interest only in the fruit of the transgenic plant organism.

In the following description, several terms are used extensively. The following definitions are provided to better define the present invention and to guide those of ordinary skill in the art in the practice of the present invention. Unless otherwise noted, terms are to be understood according to conventional usage by those of ordinary skill in the relevant art.

As used herein "chimeric gene" is a gene comprising a promoter and a coding region of different origins. In the present invention, the chimeric gene comprises the polynucleotide of the present invention linked to coding regions of endogenous and/or exogenous genes.

As used herein "consensus sequence" is an artificial sequence in which the base at each position represents the base most frequently encountered in the present sequence, when comparing different alleles, genes or organisms.

As used herein "promoter" is the DNA portion above the encoding region, which contains the sites of linkage to RNA polymerase II to initiate the transcription of the DNA.

As used herein, the term "Expression" refers to the transcription of a DNA molecule or translation of a transcribed RNA molecule of a structural gene, either endogenous or heterologous.

As used herein "GC box" is a common element in the promoter that can increase the activity of the promoter.

As used herein "TATA box" is an element in the promoter, located about 30 bases above the transcription start site. The TATA box is associated with transcription factors in general, including RNA polymerase II.

As used herein, the term "gene" refers to a physical and functional unit of heredity, represented by a DNA segment that encodes a functional protein or RNA molecule.

As used herein "endogenous gene" is a gene belonging to the cell or of the organism.

As used herein "heterologous gene" is a gene isolated from a donor organism and recombined in the transformed recipient organism. It is a gene that does not belong to the cell or organism.

As used herein, the term "reporter gene" refers to a coding unit, the product of which is easily identified, for example, genes CAT, GUS, GAL, LUC and GFP. The expression of a reporter gene may be used as an indication of the functioning of a promoter linked to this reporter gene.

As used herein, the term "propagule" refers to any part of a plant that can be used in reproduction or propagation, be it sexual or asexual, including seedlings.

As used herein, the term "sense" refers to the polynucleotide sequence in the same 5'-3' direction with respect to the promoter.

As used herein, the term "antisense" refers to the polynucleotide sequence in the contrary orientation with respect to the 5'-3' direction of the promoter.

As used herein, the term "x-mero", with reference to a specific value "x", refers to a sequence comprising at least one specific number ("x") of residues of the polynucleotide identified as SEQ ID NO:1. According to preferred embodiments, the value of x is preferably at least 20, more preferably at least 40, even more preferably at least 60 and most preferably at least 80. Thus, polynucleotides of the present invention comprise a polynucleotide of 20 meros, 40 meros, 60 meros, 80 meros, 100 meros, 120 meros, 150 meros, 180 meros, 220 meros, 250 meros, 300 meros, 400 meros, 500 meros, or 600 meros identified as SEQ ID NO:1 and variants thereof.

As used herein, the term "polynucleotide(s)" refers to a single-stranded or double-stranded polymer of desoxyribonucleotide acid or ribonucleotide acid bases and includes molecules corresponding to RNA and DNA, including HnRNA and mRNA molecules, with both "sense" and "antisense" strands, and comprises cDNA, genomic DNA, and recombinant DNA, as well as complementary or partly synthetized polynucleotides. An HnRNA molecule contains introns and corresponds to a RNA molecule containing nuclear RNA transcripts that do not end up as cytoplasmic mRNA. An mRNA molecule corresponds to a RNA molecule from which the introns were excised. A polynucleotide may consist of a complete gene, or any portion thereof.

Operable "antisense" polynucleotides may comprise a fragment of the corresponding polynucleotide, and the definition of "polynucleotide" includes all these operable antisense fragments. Antisense polynucleotides and techniques involving antisense polynucleotides are well known in the state of the art (Sambrook, J.; E. F. Fritsh and T. Maniatis—Molecular cloning. A laboratory manual, $2^{nd}$ ed., Cold Spring Harbor Laboratory Press, 1989.)

The polynucleotides described in the present invention are preferably about 80% pure, more preferably about at least 90% pure, and even more preferably about at least 99% pure.

As used herein, the term "oligonucleotide" refers to a relatively short segment of a polynucleotide sequence, generally comprising from 6 to 60 nucleotides. These oligonucleotides may be used as probes or primers, while the probes may be used in hybridization tests, the primers may be used in amplification of DNA by polymerase chain reaction.

As used herein, the term "probe" refers to a polynucleotide or nucleic acid, being RNA or DNA, occurring naturally as a digestion of a restriction enzyme, either purified or produced synthetically, which is capable of annealing with or specifically hybridizing with a nucleic acid containing sequences that are complementary to the probe. A probe may further consist of a single or a double stranded. The exact length of a probe will depend on many factors, including temperature, origin of the probe and method used. For instance, depending of the complexity of the target sequence, the oligonucleotide probe typically contains 15-25 or more nucleotides, although it may contain less nucleotides. The probes herein are selected to be complementary in order to differentiate chains from a sequence of a particular nucleic acid. This means that the probe may be sufficiently complementary to be capable of "hybridizing specifically" or annealing with its respective target-chains under a number of predetermined conditions. Consequently, the probe sequence does not need to reflect exactly the complementary sequence of the target. For instance, a non-complementary nucleotide fragment may be linked to the final 5' or 3' of the probe, with the rest of the probe being complementary to the target chain. Alternatively, non-complementary bases or long sequences may be intercalated within the probe if the latter has sufficient complementarity with the sequence of the target nucleic acid to specifically anneal with it.

As used herein, the term "primer" refers to an oligonucleotide, being either RNA or DNA, single chain or double chain, derived from a biological system, generated through digestion with restriction enzymes, or produced synthetically, which, when placed under suitable conditions, is capable of acting functionally as an initiator of the synthesis of a template-dependent nucleic acid. Such suitable conditions comprise a nucleic acid template, a polymerase enzyme, cofactors and appropriate temperature and pH, which will allow the 3 'extension of the primer by polymerase activity by adding nucleotides or with similar activity to produce a first extension of the product. A "primer' may vary in length, depending on particular conditions and requirements for application. For instance, in diagnose applications an oligonucleotide "primer" has typically from 15 to 25 or more nucleotides in length. A primer should have sufficient complementarity with the desired template to initiate the synthesis of the extension of the desired product. This does not mean that the sequence of the primer should represent an exact complement of the desired template. For example, a non-complementary nucleotide sequence may be linked to the 5' end of a complementary primer. Alternatively, non-complementary bases may be intercalated within the oligonucleotide sequence of the primer, as long as the primer has sufficient complementarity with the sequence of the desired template chain to provide a functional template-primer complex for the synthesis of the extension of the product.

AS used herein, the term "hybridizing specifically" refers to the association between two single-chain nucleic acid molecules that have sufficiently complementary sequences to enable such hybridization under pre-determined conditions, as described in the prior art (apostille: Tecnologia de DNA recombinante. Universidade de São Paulo, Capitulo 1, 2003).

In particular, this term refers to the hybridization of an oligonucleotide with a substantially complementary sequence containing a single-chain DNA or RNA molecule of the present invention. Suitable conditions required to perform specific hybridization between single-chain nucleic acid molecules of varying complementarity are well described in the prior art (apostille: Tecnologia de DNA recombinante. Unviersidade de São Paulo, Capitulo 4, 2003). A common formula for calculating the stringency conditions for having hybridization between nucleic acid molecules is given below (Sambrook et al., Molecular Cloning, A Laboratory Manual, $2^{nd}$ ed. (1989), Cold Spring Harbor Laboratory Press):

$$Tm=81.5° C.+16.6 Log [Na+]+0.41(\% G+C)-0.63(\% formamide)-600 bp \text{ in the duplex (probe)}.$$

As an illustration of the above formula, using [Na+]= [0.368] and 50% of formamide, with GC content of 42% and an average probe size of 200 bases, the Tm will be of 57° C.

Probes or primers are described as corresponding to the polynucleotide of the present invention identified as SEQ ID NO:1 or a variant thereof, if the oligonucleotide probe or primer, or the its complement, is contained within the sequence specified as SEQ ID NO:1, or a variant thereof.

As used herein, the term "oligonucleotide" refers to "primers" and "probes" of the present invention, and it is defined as a nucleic acid molecule comprising two or more ribonucleotides or deoxyribonucleotides, preferably more than three. The exact size of the oligonucleotides will depend on several factors and on the particular application and use of the oligonucleotides. Preferred oligonucleotides comprises 15-50 pairs of consecutive bases that are complementary to the SEQ ID NO:1. The probes may be easily selected by using techniques well-known in the art (Sambrook et al "Molecular Cloning, a laboratory manual", CSHL Press, Cold Spring Harbor, N.Y., 1989), as well as stringencies of DNA-DNA hybridization, recombination and melting temperatures, and the potential to form loops and other factors, which are also known in the art.

The definition of the terms "complement", "reverse complement" and "reverse sequence", as used herein, is illustrated by the following example. For the sequence 5'AGTGAAGT3', the complement is 3'TCACTTCAS', the reverse complement is 3'ACTTCACTS' and the reverse sequence is 5'TGAAGTGA3'.

As used herein, the term "variant" or "substantially similar" comprises amino acid or nucleotide sequences different from specifically identified sequences, in which one or more nucleotides or amino acid residues are deleted, replaced or added. The variants may be allelic variants, natural occurrence variants, or non-natural occurrence variants. The variant or substantially similar sequences refer to fragments of nucleic acids that may be characterized by the percentage of similarity of their nucleotide sequences with the nucleotide sequences descried herein (SEQ ID NO 1), as determined by common algorithms employed in the art. The preferred fragments of nucleic acids are those whose nucleotide sequences have at least about 40% or 45% of sequence identity, preferably about 50% or 55% sequence identity, more preferably about 60% or 65% of sequence identity, still more preferably 70% or 75% of sequence identity, still more preferably about 80% or 85% of sequence identity, stilly more preferably about 90%, 91%, 92%, 93%, 94%, 95%, 96%, 97%, 98% or 99% of sequence identity as compared with the reference sequence. The percentage identity is determined by aligning two sequences to be compared, determining the number of identical residues in the aligned portion, dividing this number by the total number of residues in the researched sequence and multiplying the result by 100. This alignment may be made by means of software existing in the Internet, one them being BLASTIN, which is available on the page of the National Center for Biotechnology Information/NCBI (ncbi.nlm.nih.gov).

As used herein, the term "vector" refers to a replicon, such as plasm ide, cosmide, bacmide, fagus or virus, in which other genetic sequences or elements (be it DNA or RNA) can be linked and replicated together with the vector. Preferably, the vector is derived from a virus selected from bacteriophages, vaccine virus, retrovirus or bovine papilloma virus. The "recombinant vector" results from the combination of a commercial vector with chimeric genes, or the polynucleotide of the present invention, operationally linked to an endogenous and/or heterologous polynucleotide of interest, which in turn, is operationally linked to a termination signal. Such vectors can be obtained commercially, from Clontech Laboratories, Inc (Palo Alto, Calif.), Stratagene (La Jolla, Calif.), Invitrogen (Carlsbad, Calif.), New England Biolabs (Beverly, Mass.) and Promega (Madison, Wis.). A few examples of vectors used in the present invention, but not limited to, the vectors pGEM-T, pCAMBIA 1391, gateway vectors and the pMON.

As used herein, the term "expression enhancing sequences" refers to "enhancers", which may be distant from the promoter (upstream or downstream) and that potentiate the transcription rates. These enhancers are not specific and potentiate the transcription of any promoter in there vicinity. The efficiency of the expression of a gene in a specific tissue depends on the adequate combination and integration of the enhancers, promoters and adjacent sequences.

The first enhancer discovered, which stimulated the transcription of eukaryote genes was the SV40 (present in the genome of the Virus 40 of Apes). After the discovery of the SV40enhancer, hundreds of other enhancers were identified, as for example, HSV-1, AMV, HPV-16, in other viral genomes in the DNA of eukaryotic cells. (Lodish et al, Biologia celular e molecular. 4$^a$ edição page 368)

The expression "operationally linked" means that the regulatory sequences necessary for the expression of the coding sequence are placed in the DNA molecule in appropriate positions with respect to the coding sequence for expression of the coding sequence. The same definition is often employed for the arrangement of coding sequences and controlled elements of the transcription (for example, promoters, aids or enhancers and elements or termination sequences) in the expression vector. An exogenous coding region is typically flanked by operationally linked regulatory regions that regulate the expression of the exogenous coding region in a transformed cell (which may be a microorganism, either vegetable or animal). A typical regulatory region operationally linked to an exogenous coding region includes a promoter, that is, a nucleic acid fragment that may cause transcription of exogenous coding regions, positioned in region 5' of the exogenous coding region. In the case of the present invention, the regulatory region refers to the regions substantially similar to the SEQ ID NO. 1. IN order to aid in increasing the transcription of a determined polynucleotide, he promoter sequence of the present invention may be linked to other regulatory sequences already described, such as: ATATT (an element of strong expression in the root), AACAAAC and GCCACCTCAT (SEQ ID NO: 10) (elements relating to the expression in seeds), CACGTG and CCTACC (both sequences can be stimulated to a stress factor), among others. (Ai-Min Wu et al, Isolation of a cotton reversibly glycosylated polypeptide (GhRGP1) promoter and its expression activity in transgenic tobacco, Journal of Plant Physiology 163 (2006) 426-435).

A "termination sequence" is a DNA sequence that signals the end of the transcription. Examples of termination include, but are not limited to, the termination signal of SV40, the adenylation signal of HSV TK, termination signal of the nopaline synthase gene of *Agrobacterium tumefaciens* (NOS), termination signal of the 19S gene and 35S of CaMV, termination signal of the maize alcohol dehydrogenase, termination signal of the manopine synthase gene, termination signal of the beta-faseoline gene, termination signal of the ssRUBISCO gene, termination signal of the sucrose synthase gene, termination signal of the virus that attacks *Trifolium* subterranean (SCSV), termination signal of the trpC gene of *Aspergillus nidulans*, among others. The present invention provides an isolated polynucleotide regulatory region that may be used for manipulating plant phenotypes. More specifically the present invention relates to the promoter or regulatory sequence according to SEQ ID NO:1, responsible for the expression of a LTP1 ("Lipid Transfer Protein") family representative, called in the present invention CaLTP1, responsible for the expression in the fruit endosperm.

The amount of a polypeptide of specific interest may be increased or reduced by incorporating additional copies of genes, or coding sequences, coding the polypeptide, operationally linked to the promoter sequence of the present invention (SEQ ID NO:1), in the genome of an organism, such as a plant. Similarly, an increase or decrease in the amount of the polypeptide can be achieved by transforming the plant with anti-sense copies of these genes.

The polynucleotide of the present invention was isolated from coffee plants, more specifically *Coffea arabica*, but it may be alternatively synthetized by using conventional synthesis techniques. Specifically, the isolated polynucleotide of the present invention includes the sequence identified as SEQ ID NO:1; the complement of the sequence identified as SEQ ID NO:1; the reverse complement of the sequence identified as SEQ ID NO:1.

The polynucleotide of the present invention may be identified in plant genomic DNA sequences, which the information of the genome sequence is available to the public, or it may be isolated from various polynucleotide libraries, or synthetized by using techniques that are well known in the art (Sambrook et al "Molecular Cloning, a laboratory manual", CSHL Press, Cold Spring Harbor, N.Y., 1989). The polynucleotide may be synthetized, for example, by using automatized oligonucleotide synthesizers (for example, DNA OLIGO 1000M synthesizer Beckman) to obtain polynucleotide segments of up to 50 or more nucleic acids. A plurality of these polynucleotide segments may then be linked by using standard DNA handling technique that are well known in the art (Sambrook et al "Molecular Cloning, a laboratory manual", CSHL Press, Cold Spring Harbor, N.Y., 1989). A conventional polynucleotide synthesis technique involves the synthesis of a single-stranded polynucleotide segment, having, for example, 80 nucleic acids, and hybridizing this segment to a complementary segment of 85 nucleic acids, synthetized, to produce an overhang of 5 nucleotides. The next segment may then be synthetized in a similar manner, as an overhang of 5 nucleotides in the opposite strand. The "sticky" or cohesive ends ensure an appropriate linkage when the two portions are hybridized. In this way, the polynucleotide of this invention may be synthetized completely in vitro.

As observed above, the promoter sequence of the present invention may be used in recombinant and/or expression vectors to drive the transcription and/or expression of a polynucleotide of interest. The polynucleotide of interest may be endogenous or heterologous to an organism, for example, a plant, to be transformed. The recombinant and/or expression vectors of the present invention may then be employed to modulate the levels of transcription and/or expression of a polynucleotide, for example, a gene that is present in the wild-type plant, or may be employed to drive transcription and/or expression of a DNA sequence that is not found in the wild-type plant, including, for example, a gene that encodes a reporter gene, such as GUS.

In some embodiments, the polynucleotide of interest comprises an open reading frame that encodes a polypeptide of interest. The open reading frame is inserted into the vector in a sense orientation and the transformation with this genetic construct/recombinant vector will generally result in overexpression of the selected polypeptide. The polypeptide of interest, which will be regulated by the promoter of the present invention, may be inserted into the vector in the sense orientation, antisense orientation, or both directions. The transformation with a recombinant vector and/or expression vector containing the promoter of the present invention will drive the regulation of the expression of the polynucleotide of interest in the antisense orientation or in both orientations (sense and antisense), generally resulting in the reduced expression of the selected polypeptide.

The polynucleotide of interest, as a coding sequence, is operatively linked to the polynucleotide promoter sequence of the present invention, making a host cell capable of transcribing a targeted RNA by the promoter sequence linked to the polynucleotide of interest. The polynucleotide promoter sequence is generally positioned at the 5' end of the polynucleotide to be transcribed. The use of a tissue-specific promoter, like the coffee promoter sequence (*Coffea arabica*), responsible for the expression of the LTP1 (Lipid Transfer Protein) gene identified as SEQ ID NO: 1, will affect the transcription of the polynucleotide of interest only in the endosperm of the transformed plant.

The recombinant vector or expression vector of the present invention may also contain a selection marker that is effective in the organism cells, such as a plant, to enable detection of transformed cells containing the inventive recombinant vector. These markers, which are well known, typically gives resistance to one or more toxins. One example of this marker is the nptII, which expression results in resistance to kanamycin or neomycin, antibiotics that are generally toxic to plant cells in moderate concentration. Thus, transformed cells can be identified for their capability of growing in a medium containing these antibiotics. Other markers that may be used for constructing recombinant vectors and/or expression vectors containing the polynucleotide of the present invention may be, without limitation thereto: the hpt gene, that imparts resistance to the hygromycin antibiotic; the manA gene and the bar gene.

The system that uses the manA gene (which encodes the PMI (phosphomannose isomerase) enzyme) of *Escherichia coli* (Miles and Guest, 1984. Complete nucleotide sequence of the fumarase gene fumA, of E. coll. Nucleic Acids Res. 1984 Apr. 25; 12(8): 3631-3642) has mannose as a selective agent, being one of the new systems suggested as alternatives to the first two described above (Joersbo et al., 1998. Parameters interacting with mannose selection employed for the production of transgenic sugar beet, Physiologia Plantarum, Volume 105, Issue 1, Page 109—January 1999 doi: 10.1034/j.1399-3054.1999.105117.x). The plant species that do not metabolize mannose undergo severe growth inhibition when the latter is offered as the only source of carbon in a culture medium. The adverse and inhibitory effects of the use of mannose are consequences of the accumulation of mannose-6-phosphate, a product of the phosphorylation of mannose by hexokinase. PMI promotes the interconversion of mannose-6-phosphate and fructose-6-phosphate, thus enabling the former to be catabolized in the glycolytic pathway (Ferguson e Street, 1958. Análise de sistemas gene marcador/agente seletivo alternativos para seleção positive de embriões somáticos transgênicos de mamoeiro, *Rev. Bras. Fisiol. Veg.,* 2001, vol. 13, no. 3, p. 365-372. ISSN 0103-3131: Malca et al., 1967 Advances in the selection of transgenic plants using non-antibiotic marker genes, Physiologia Plantarum, Volume 111, Issue 3, Page 269—March 2001 doi:10.1034/j.1399-3054.2001.1110301.x). The bar gene (which encodes the PAT (phosphinothricin-N-acetyltransferase) enzyme) of *Streptomyces hygroscopicus* (Murakani et al., 1986—The bialaphos biosynthetic genes of *Streptomyces hygroscopicus*: molecular cloning and characterization of the gene cluster. Molecular and General Genetics., 205: 42-50, 1986.) has the glufosinate ammonium (PPT) as a selective agent, being, among the herbicide-tolerance gene systems type, one of the most widely employed by genetic engineering in the development of plant GMO (genetically modified organism). PAT inactivates herbicides that exhibit PPT as an active compound by detoxification thereof. Detoxification, which results from acetylation of the free amino group present in the PPT, makes the latter incapable of competing, in an inhibitory way, with glutamine synthetase (GS), thus enabling the removal of the toxic ammonia from the plant cell by converting glutamate into glutamine, which reaction is catalyzed by GS (Lindsey, 1992 Molecular cloning of ICAM-3, a third ligand for LFA-1, constitutively expressed on resting leukocytes, *Nature* 360, 481-484 (3 Dec. 1992); doi: 10.1038/360481a0).

Alternatively, the presence of the chimeric gene in transformed cells may be determined by other techniques well known in the art (Sambrook et al "Molecular Cloning, a laboratory manual", CSHL Press, Cold Spring Harbor, N.Y., 1989), such as Southern blot and PCR.

The techniques for operatively linking the components of the recombinant vectors or expression vectors are well known in the art and include the use of synthetic ligands containing one or more restriction endonuclease sites, as described, for example, in Sambrook, et al. ("Molecular Cloning, a laboratory manual", CSHL Press, Cold Spring Harbor, N.Y., 1989). Chimeric genes of the present invention may be linked to a vector having at least one replication system, for example, *E. coli*, so after each manipulation, the resulting constructs may be cloned and sequenced.

Recombinant vectors and/or expression vectors of the present invention may be used for transforming a variety of organisms, including, but not limited to plants. Plants that may be transformed by using recombinant vectors and/or expression vectors of the present invention include monocotyledonous angiosperms (for example, grasses, maize, grains, oat, barley), dicotyledonous angiosperms (for example, *Arabidopsis*, tobacco, legumes, alfalfa, barley, eucalyptus, maple . . . ), and gymnosperms (for example, pine tree, white spruce, larch . . . ). The plant transformation protocols are already well known in the art (Manual de transformação genética de plantas. Brasilia: EMBRAPA-SPI/EMBRAPA-CENARGEM, Capitulo 3 e 7, 1998). In another preferred embodiment, the recombinant vectors and/or expression vectors of the present invention are employed to transform dicotyledonous plants. Preferably, the plant is selected from the Rubiaceae family, more preferably of *Coffea arabica* species. Other plants may be transformed with the recombinant vector and/or expression vector of the present invention, including, but not limited to: *Anacardium, Anona, Arachis, Artocarpus, Asparagus, Atropa, Avena, Brassica, Carica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoseyamus, Lactuca, Linum, Lolium, Lupinus, Lycopersicon, Malus, Manihot, Majorana, Medicago, Nicotiana, Olea, Oryza, Panieum, Pannesetum, Passiflora, Persea, Phaseolus, Pistachia, Pisum, Pyrus, Prunus, Psidium, Raphanus, Ricinus, Secale, Senecio, Sinapis, Solanum, Sorghum, Theobromus, Trigonella, Triticum, Vicia, Vitis, Vigna,* and *Zea*.

The transcription termination signal and the polyadenylation region of the presente invention includes, but not limited to, the termination signal of SV40, the adenylation signal of HSV TK, termination signal of the nopaline synthase gene of *Agrobacterium tumefaciens* (nos), termination signal of the RNA 35S gene of CaMV, termination signal of the virus that attacks *Trifolium* subterranean (SCSV), termination signal of the trpC gene of *Aspergillus nidulans*, among others. Preferably, the terminator used in the present invention is the LTP1 (Lipid Transfer Protein) gene terminator.

The recombinant and/or expression vector of the present invention may be introduced into the genome of the desired host plant by a number of conventional techniques. For example, *A. tumefaciens*; electroporation; protoplast fusion; injection into reproductive organs; injection into immature embryos; microinjection of protoplast of plant cells; by using ballistic methods, such as bombardment of DNA-covered particles, and others. The choice of the technique will depend on the plant to be transformed. For instance, dicotyledonous plants and some monocotyledonous and gymnosperm plants can be transformed by the technology of *Agrobacterium* Ti-plasmid. The recombinant and/or expression vector may be combined with appropriate T-DNA flanked regions and introduced into a conventional host vector like *A. tumefaciens*. The virulence of the host *A. tumefaciens* will direct the insertion of the genic constructs and adjacent markers within the plant cell DNA when the cell is infected by the bacterium. The transformation technique mediated by *A. tumefaciens*, including disarmament and the use of binary vectors, are well described in the scientific literature (as mentioned in patent application US 20020152501, Horsch et al. Science 233:496-498, 1984; and Fraley et al. Proc. Natl. Acad. Sci. USA 80:4803, 1983). The binary vector preferably used in the present invention is the pBI-121-type binary vector.

Microinjection techniques are known in the art and are well described in the scientific and patent literature. The introduction of recombinant and/or expression vectors by using polyethylene glycol precipitations is described in Paszkowski et al. Embo J. 3:2717-2722, 1984 (as mentioned in patent application US20020152501). Electroporation techniques are described in From et al. Proc. Natl. Acad. Sci. USA 82:5824, 1985 (as mentioned in patent application US20020152501). Ballistic transformation techniques are described in Klein et al. Nature 327:70-73, 1987 (as mentioned in patent application US20020152501). The introduction of recombinant and/or expression vectors of the present invention may be made in tissues, such as leaf tissue, dissociated cells, protoplasts, seeds, embryos, meristematic regions, cotyledons, hypocotyledons, and others. Preferably, the present invention uses the transformation via *A. tumefaciens* using *A. thaliana* as a model plant (Clough et al., "Floral dip: a simplified method for *Agrobacterium*-mediated transformation of *A. thaliana*", Plant J. 1998 December; 16(6):735-43). However, other transformation methods may be used for inserting recombinant and/or expression vectors of the present invention, such as the biolistic, which consists of a DNA transformation technique that uses microprojectiles propelled at high speed to carry the DNA into the cells (Rech, E. L; Aragão, F. J. L. Biobalística. In: Manual de Transformação Genética de Plantas (Brasileiro, A. C. M. & Carneiro, V. T. C. eds.), EMBRAPA Servico de Produção de Informações —SPI. 1998, 106 pp), and the pollen tube transformation. The method of pollen tube transformation was disclosed for the first time by Zhou et al. (Zhou, G., Wang, J., Zeng, Y., Huang, J., Qian, S., and Liu, G. Introduction of exogenous DNA into cotton embryos. Meth. in Enzymol. 101:433-448, 1983) and consists in applying a DNA solution to the upper portion of a young apple after pollination. By using this technique, the exogenous DNA may reach the ovary through the passage left by the pollen tube and integrate the already fertilized zygotic cells, but not divided.

Once the cells have been transformed, by any of the technique mentioned above, the cells having the recombinant and/or expression vectors of the present invention incorporated in their genome may be selected by a marker, such as the marker that gives resistance to hygromycin or kanamycin. The transformed plant cells may then be cultivated to regenerate a whole plant having the transformed genotype and, finally, the desired phenotype. Such regeneration techniques rely on the manipulation of certain phytohormones through the tissue culture growth medium, typically containing a biocidal and/or herbicide marker, which should be introduced together with the desired nucleotide sequence. Regeneration of plants from protoplast culture is described in Evans et al. (Evans et al, Protoplasts Isolation and Culture, Handbook of Plant Cell Culture, pp. 124-176, MacMillilan Publishing Company, New York, 1983; e Binding, Regeneration of Plants, Plant Protoplasts, pp. 21-73, CRC Press, Boca Raton, 1985, as mentioned in patent application US20020152501). The regeneration may also be achieved through plant callus, explants, or parts thereof. Such regeneration techniques are well known in the art as shown in Leelavathi et al. [Leelavathi et al, A simple and rapid *Agrobacterium*-mediated transformation protocol for cotton (*G. hirsutum* L.): Embryogenic calli as a source to generate large numbers of transgenic plants, Plant Cell Rep (2004) 22:465-470]. This paper describes a protocol for cotton transforming and regenerating, wherein the embryogenic callus containing the *Agrobacterium* is cultivated under dehydration stress and antibiotic selection for 3 to 6 months for regeneration of various transgenic embryos, with an average of 75 globular embryos. After being observed on the plate selection, these embryos are grown and multiplied in the medium, followed by the development of cotyledon embryos on the embryo maturation medium. In order to obtain an average of 12 plants by Petri dishes of co-cultivated calluses. Approximately 83% of these plants are transgenic. The resulting transformed plants can be reproduced sexually or asexually, by using methods known in the art (Leelavathi et al., A simple and rapid *Agrobacterium*-mediated transformation protocol for cotton (*Gossipium hirsutum* L.): Embryogenic calli as a source to generate large numbers of transgenic plants, Plant Cell Rep, 2004, 22: 465-470), to provide successive generations of transgenic plants.

The cell RNA production can be controlled by selection of the promoter sequence, by selection of the number of functional copies or through the integration site of the polynucleotide incorporated into the host genome. An organism may be transformed by using a recombinant and/or expression vector of the present invention containing more than one coding open reading frame for a polypeptide of interest.

The isolated polypeptide of the present invention has also use in mapping the genome, in physical mapping and in positional cloning of genes. The sequence identified as SEQ ID NO: 1 and variants thereof can be used for designing probes and oligonucleotide primers. The oligonucleotide probes designed by using the polynucleotide of the present invention can be used for detecting the presence of the promoter of the LTP1 gene in any organism having DNA sequence that are sufficiently similar in their cells, by using well known techniques in the art, such as the dot blot DNA hybridization technique (Sambrook, J., Fritsch, E. F., Maniatis, T. Molecular cloning a laboratory manual. $2^{nd}$ edition [M]. New York: Cold Spring Harbor Laboratory Press, 1989).

The oligonucleotides designed by using the polynucleotide of the present invention can be used for PCR amplifying. The polynucleotide of the present invention can also be used for labeling or identifying an organism or reproductive material thereof. This label can be obtained, for instance, by stable introduction of an identifier of heterologous, non-functional, non-disruptive polynucleotide in an organism, under control of the polynucleotide of the present invention.

The promoter proposed for the present invention has been obtained by following preferably the steps cited hereinafter.

1—The genetic material of the samples of possible candidates can be obtained according to the procedures described by Jones (Jones J D G, Dunsmuir P, e Bedbrook J. 1985. High level expression of introduced chimeric genes in regenerated transformed plants, EMBO J 4: 2411-2418), or any procedure that enables access to the whole genetic material, as for example, the extraction methods that use organic solvents.

2—The integrity of the isolated material of the possible candidates should be confirmed, as for instance, through denaturing gel techniques, and then serving as a template to form the new DNA molecules by PCR reactions, or RT-PCR, if the template is RNA. It is recommended the treatment of the samples with DNAse, as for instance, via the procedure described herein.

3—The genetic material obtained can be used in PCR reactions as specific primers of selected genes, as for example, the LTP1 gene, for evaluation of the specificity thereof. The said primers can be designed with the aid of the program Primer (frodo.wi.mitedu/primer3/) (Rozen, S and Skaletsky H. J. 2000 Primer3 on the WWW for general users and for biologist programmers. In: Krawetz S, Misener S (eds) Bioinformatics Methods and Protocols: Methods in Molecular Biology. Humana Press, Totowa, N.J., pp 365-386), or any other program and/or process that provides specific primers for the candidates.

4—The PCR reactions can be conducted on a special apparatus for the procedure, such as MJ Research model PTC-100 thermocycler, or any other thermocycler capable of developing its function in ideal conditions for the reaction, and it is suggested an initial incubation at 94° C. for 3 minutes, followed by 35 cycles at 94° C. for 30 seconds for denaturation, 40 seconds at 50° C. for hybridization of the oligonucleotides and 1 minute at 72° C. for extension.

5—After the procedure, the reactions should be subjected to an additional period, it is recommended 10 minutes at 72° C., for completing polymerization. It is recommendable that each reaction should contain 1 µL of diluted cDNA (1:10), 2.5 U of Taq DNA polymerase and 30 pmoles of initiating oligonucleotides in a final volume of 50 µL.

6—The identity of the amplified product can be confirmed, as for instance, by electrophoretic migration of the fragments, in which it is recommended using, as a comparison, the positive control, constituted by a vector, as for example, a databank vector of the *Projeto Genoma Café* (Coffee-Genome Project) (FV2-050) containing the sequence being studied.

7—After fractioning the genetic material, the samples should be subjected to the Northern Blot process, wherein it is recommended transferring the genetic material to a membrane suitable for the procedure, as for example, a nylon membrane; and hybridizing the genetic material in SSPE with a probe corresponding to the partial sequence of the alleged LTP marked, as for example, a marked one with the isotope 32 of phosphorus ($^{32}P$).

8—The promoter should be isolated by any isolation technique, in which it is recommended using the 5' race technique, coupled with the nested PCR technique simplified by using the Genome Walker Universal Kit (Clontech) according to specification of the manufacturer.

9—The in-coming fragments can be cloned and sequenced by a process intended for this purpose. It is recommended the use of a dideoxynucleotide method (Sanger, F., Nicklen, S. and Coulson, A. R. 1979. Proc. Natl. Acad. Sci. USA, 74, 5463-5468).

10—The characterization of the expression profile of the isolated putative promoter can be carried out through the expression of its sequence, and truncated variations coming from it, but that preserve the proposed function of a promoter, in binary vectors, wherein it is suggested the use of the pBI 121 type binary vector and cloning at the sites Hind III and Bain HI according to molecular biology standard technique, as for example the technique proposed by Sambrook (SAMBROOK, J.; FRITSCH, E. F.; MANIATIS, T. Molecular. Cloning: A Laboratory Manual 1. 2. ed. New York: Cold Spring Harbor Laboratory Press, 1989. 608p). It is recommended the use of positive and negative controls for carrying out these processes.

11—The transformation process should be carried out in the organism of interest, for which it is suggested the tobacco—*Nicotiana tabacum*, by using, as a vector, *Agrobacterium tumefaciens* strains, as for example the CV3101 (C58PMP90) strain of *Agrobacterium tumefaciens*, using any specific protocol for this purpose, as for example that proposed by Horsch (Horsch R. B., Fry J. B., Hoffman N. L., Eicholts D., Rogers S. G. and Fraley R. T. 1985. A simple and general method for transferring genes into plants. Science 227: 1229-1231). The efficiency of transforming the explants should be evaluated through the transient and stable expression in the tissues of the regenerated propagules of a gene of interest, wherein it is recommended the use of the GUS gene.

12—The analysis of GUS gene expression should be carried out by histochemical assay protocols, as for example, according to adaptation of the protocol described by Jefferson (Jefferson R. A., Kavangh T. A. and Bevan M. W. 1987. GUS fusions: β-glucuronidase as a sensitive and versatile gene fusion marker in higher plants—EMBO J. 6: 3901-3907) in leaves, roots, fruits, seeds and flowers (petals, gynoecium, stamen, pollen) of the transformed plants.

EXAMPLES

The present invention is further defined in the following examples. It should be understood that these Examples, while indicate a part of the invention, are given only as illustration, without being limitative of the scope of the present claims.

Usual molecular biology techniques such as transformation of bacteria and agarose gel electrophoresis of nucleic acids are referred to by common terms to describe them. Details of the practice of these techniques, well known in the art, are described in Sambrook, et al. (Molecular Cloning, A Laboratory Manual, $2^{nd}$ ed. (1989), Cold Spring Harbor Laboratory Press). Various solutions used in experimental manipulations are referred to by their common names, such as "agarose", TBE", "miniprep", etc. The compositions of these solutions can be found in the reference Sambrook, et al. (cited above).

Example 1—in Silico Analysis

The "contigs" of the databank of the coffee genome (VIEIRA, L. G. E. ANDRADE, A. C.; COLOMBO, C. A.; MORAES, A. H. A.; MEHTA, A.; OLIVEIRA, A. C.; LABATE, C. A.; MARINO, C. L.; MONTEIRO-VITORELLO, C. B. Brazilian coffee genome project: an EST-based genomic resource. Brazilian Journal of Plant Physiology, v. 18, p. 95-108, 2006) were organized in two contrasting groups: fruit and non-fruit. These two groups were compared by means of Fisher exact test, and the result indicated 18 "contigs" preferably expressed in the fruit. Then the "contigs" were analyzed for the existence or non-existence of patents.

Example 2—Experimental Validation

A "contig" called fruit candidate gene 1—CaLTP1 was selected for experimental validation, because it exhibited a high degree of specificity and high level of expression exclusive in fruit, and because it is not protected by a patent, either the gene neither its promoter. After the characterization and validation tests, it was clear that it was the LTP (Lipid Transfer Protein) gene. The experimental validation of the CaLTP1 gene (fruit candidate gene 1) was carried out as described by means of temporal and spatial expression assays using the RT-PCR (Reverse Transcriptase-PCR), Northern Blot; RT-qPCR techniques.

Example 3—RT-PCR

For carrying out the RT-PCR assays, RNA samples were extracted from root, leaf and fruit of *Coffea arabica* cv IAPAR 59, cultivated in the experimental field of the Embrapa Cerrados. The RNA was extracted according to the methodology described by Jones (Jones J D G, Dunsmuir P, and Bedbrook J. 1985. High level expression of introduced chimeric genes in regenerated transformed plants. EMBO J 4: 2411-2418). Then the RNAs were evaluated for their integrity in denaturing gel 1.5%. The root, leaf, and fruit RNA samples were used as template in the formation of cDNA molecules by RT-PCR reactions using oligo dT primers. The cDNAs obtained were used in PCR reactions with LTP1-specific primers for evaluation of tissue specificity thereof. For this purpose, it was developed the following specific oligonucleotides with the aid of the program Primer (frodo.wi.mit.edu/primer3/) (Rozen, S e Skaletsky H. J. 2000 Primer3 on the WWW for general users and for biologist programmers. In: Krawetz S, Misener S (eds) Bioinformatics Methods and Protocols: Methods in Molecular Biology. Humana Press, Totowa, N.J., pp 365-386):

Primer for fruit n° 1: SEQ ID NO: 2;
Primer for fruit n° 2: SEQ ID NO: 3.

Figure 2:
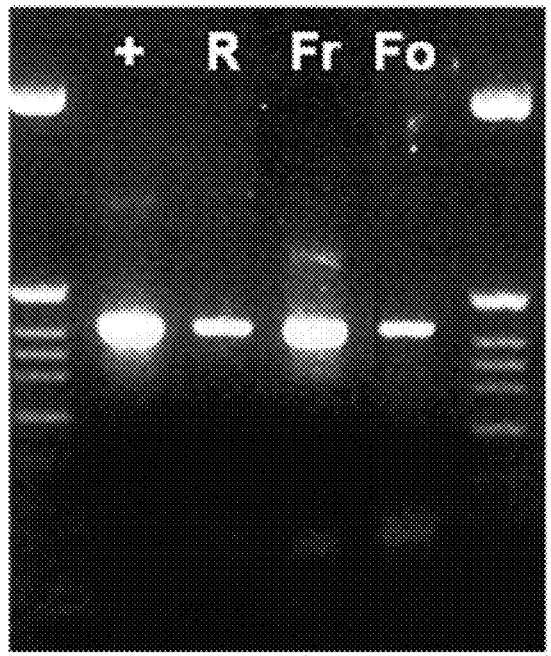
FIG. 2—the electrophoretic fractioning of specific fragments representing the sequence of CaLTP1 (*Coffea arabica* Lipid Transfer Protein 1). (+) positive control, (R) root DNA, (Fr) fruit DNA and Fo) leaf DNA.

The reactions were conducted in a MJ Research model PTC-100 thermocycler, with initial incubation at 94° C. for 3 minutes, followed by 35 cycles at 94° C. for 30 seconds for denaturation, 40 seconds at 50° C. for hybridization of the oligonucleotides and 1 minute at 72° C. for extension. After the cycles, the reactions were subjected to an additional period of 10 minutes to 72° C. for completing the polymerization. Each reaction contained 1 μL of diluted cDNA (1:10), 2.5 U of Taq DNA polymerase and 30 pmoles of initiating oligonucleotides in a final volume of 50 μL. The identity of the amplified product was confirmed by electrophoretic migration of the fragments as compared to the positive control, constituted by a vector from the data bank of the *Projeto Genoma Café* (Coffee Genome Project) (FV2-050) containing the sequence being studied (FIG. 2).

Example 4—Extraction of RNA

RNA samples of total root, leaf and fruit of *Coffea arabica* cv IAPAR 59, cultivated in the experimental field of the Embrapa Cerrados, were extracted following the protocol described by Jones (Jones J D G, Dunsmuir P, and Bedbrook J. 1985. High level expression of introduced chimeric genes in regenerated transformed plants, EMBO J 4: 2411-2418). After being extracted, the RNAs were fractioned in denaturing gel 1.5% for analysis of its integrity.

Example 5—DNAse Treatment

The RNAs were subjected to the treatment with the enzyme DNAse, which consisted of a reaction containing 10 μg of the RNAs, 5 U of the DNAse enzyme, 2 μL of the reaction buffer 10× (200 mM Tris-HCl pH 8, 0.1 mM EDTA, 1 mM DTT) and DEPC water for completing the volume of 20 μL. The reaction was incubated at 37° C. for 10 minutes and then transferred to the ice. After the reaction, the samples were treated for the purpose of activating the DNAse, that is, it was added 180 μL DEPC water and 200 μL chlorofane (24:24:1 of phenol, chloroform, and isoamyl alcohol, respectively). After mixing a few times, the samples were centrifuged at 12.000 g for 3 minutes. The upper phase (aqueous) was transferred to a new tube and ethanol (2.5 times sample volume) and NaAc 3M (1/10 sample volume) were added and incubated at −20° C. for about 16 h. Then the samples were centrifuged at 12.000 g for 40 minutes, the supernatant was discarded, and the pellet was washed with 70% ethanol before being resuspended in 20 μL of DEPC water. After treatment, isolated RNA samples were placed on 1.5% agarose gel for analysis of their quality.

Example 6—cDNA Synthesis

The cDNA synthesis reaction was carried out with 300 ng of root, leaf or fruit RNA (treated with DNAse), 2 μL of oligo dT (50 μM), 1 μL of dNTP Mix (15 mM) and DEPC water until completing 13 μL. The reaction was heated up to 65° C. for 5 minutes and then placed into the ice for 3 minutes. Then, it was added 4 μL of First-Strand Buffer (5×), 1 μL of DDT (0.1 M) and 1 μL of SuperScript III RT (200 U/μL). The reaction was incubated at 50° C. for 1 hour and then at 70° C. for 15 minutes for activating the reaction.

Example 7—RT-qPCR

Figure 3:
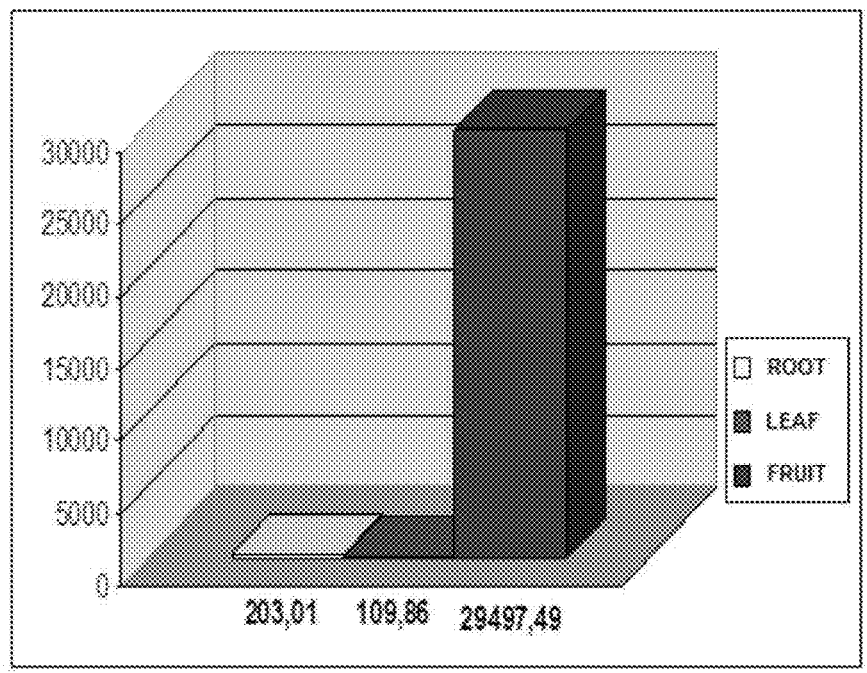
FIG. 3—a graph representing the expression profile of the LTP1 in root, leaf and fruit normalized by the ubiquitin gene.

Total root, leaf and fruit RNA samples were treated with DNase and converted to cDNA. The PCR reactions were prepared by using the SYBR Green reactant, and the following specific oligonucleotides:
Primer for fruit n° 3: SEQ ID NO: 4;
Primer for fruit n° 4: SEQ ID NO: 5.
The reactions were conducted on the 7500 PCR Systems (Applied Biosystems) according to Bustin, (Bustin SA in Quantification of mRNA using real-time reverse transcription FOR (RT-PCR): trends and problems; J Mol Endocrinol (2002) v. 29—p 23-39). The comparative analyses were made by using the ubiquitin gene as a constitutive standard (FIG. 3).

Example 8—Northern Blot

Figure 4:
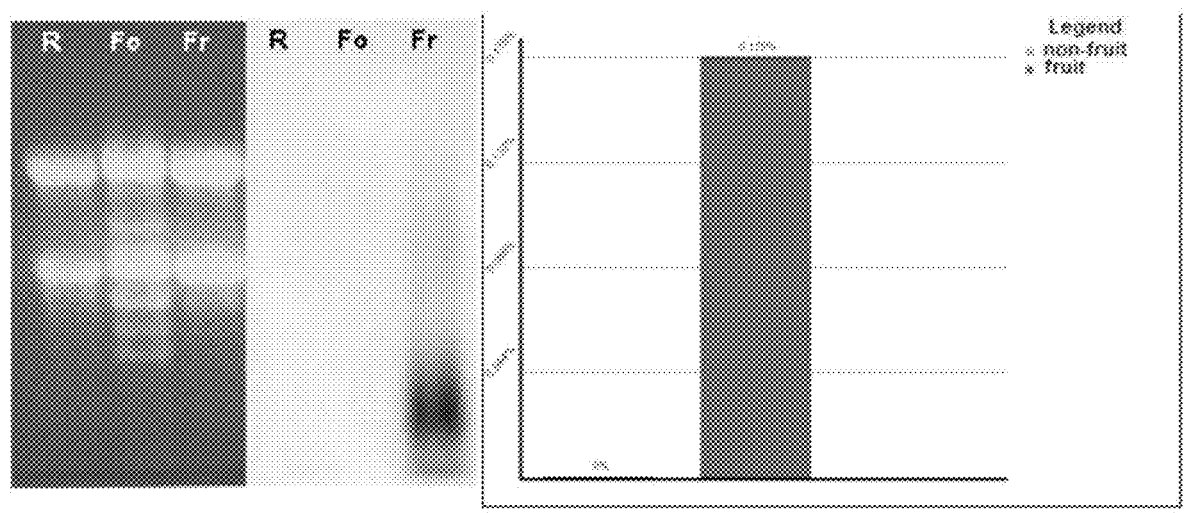
FIG. 4—Northern Blot validation of the preferred expression of LTP1 in fruit. Denaturating gel 1.5% with samples of root, leaf and fruit of *Coffea arabica* 120 days after flowering; R=root, Fo=leaf, Fr=fruit.

Total leaf and fruit (unripe stage) RNA samples were extracted from *Coffea arabica* adult coffee plant, Yellow-Catuaí variety. In the case of the root, it was used plant roots 190 days after germination on germitest paper, transferred to a plant substrate (vermiculite—Terral) and cultivated in greenhouse. The RNA extraction method was described by Jones (Jones J D G, Dunsmuir P, e Bedbrook J. 1985. High level expression of introduced chimeric genes in regenerated transformed plants. EMBO J 4: 2411-2418). The RNA was fractioned in 1.5% denaturing gel and vacuum transferred for a nylon membrane, hybridized in SSPE with a probe corresponding to the partial sequence of the alleged $^{32}P$ marked LTP. The result achieved in the experimental validation by Northern blotting demonstrates the fruit-specific gene expression (FIG. 4).

Example 9—Promoter Isolation

Figure 5:
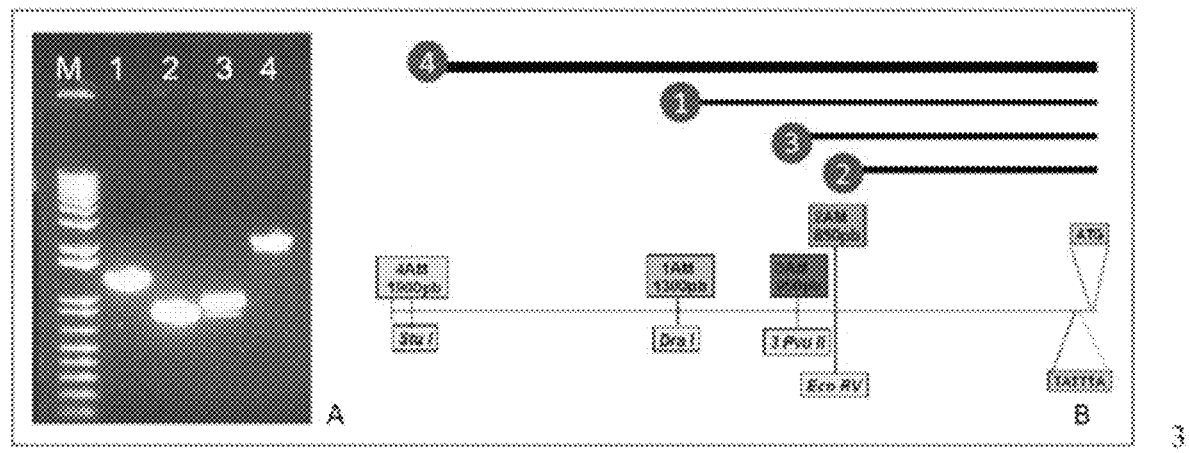
FIG. 5—electrophoretic fractioning of the fragments obtained by means of the 5' race technique. M—marker 1 Kb ladder, 1/1M—Dral library, 2/2M—Eco RV library, 3/3M—Pvull library and 4/4M—Stul library.
Figure 6:
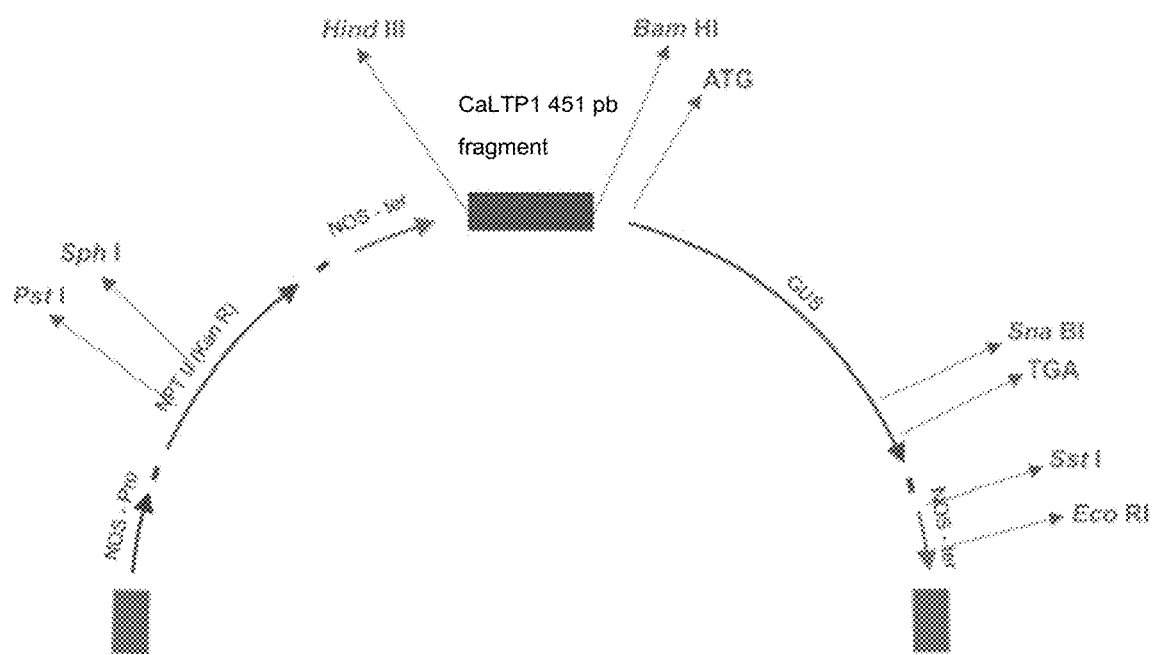
FIG. 6—binary factor PBI121 including a 451 pb fragment of promoter CaLTP1.

The promoter was isolated by the 5' race technique, coupled with the nested PCR technique, simplified by the use of the Genome Walker Universal Kit (Clontech) according to the specifications of the manufacturer. For amplification, the following primers were used:
$1^{st}$ reaction:
Primer for $1^{st}$ forward reaction: SEQ ID NO: 6;
Primer for $1^{st}$ reverse reaction: SEQ ID NO: 7.
$2^{nd}$ reaction:
Primer for $2^{nd}$ forward reaction: SEQ ID NO: 8;
Primer for $2^{nd}$ reverse reaction: SEQ ID NO: 9.
The fragments obtained (FIG. 5) were cloned and sequenced by the dideoxynucleotide method (Sanger, F., Nicklen, S. and Coulson, A. R. 1979. Proc. Natl. Acad. Sci. USA, 74, 5463-5468).

Example 10—Obtainment of Binary Vectors

In order to characterized the expression profile of the isolated putative promoter, it was made four binary vectors containing the complete version of the CaLTP1promote, which is a fragment of 1.2 Kb and three truncated versions of 451 bp, 785 bp and 1.0 Kb. For this purpose, the fragments were cloned in a pBI 121 binary vector at the sites Hind III and Bam HI according to the molecular biology standard techniques (SAMBROOK, J.; FRITSCH, E. F.; MANIATIS, T. Molecular. Cloning: A Laboratory Manual 1. 2. ed. New York: Cold Spring Harbor Laboratory Press, 1989. 608p).

Example 11—Transformation of Tobacco with Binary Vectors

The binary vectors according to the preceding item were used for transforming tobacco plants. *Agrobacterium tumefaciens* CV3101 (C58PMP90) strains were transferred independently with the four constructs cited in the preceding item, as well as with the original positive control pBI 121 according to Horsch (Horsch R. B., Fry J. B., Hoffman N. L., Eicholts D., Rogers S. G. and Fraley R. T. 1985. A simple and general method for transferring genes into plants. Science 227: 1229-1231). Following this step, the foliar sections (explants) of *Nicotiana tabacum* were dipped into a bacterial suspension containing the binary vector for 5 minutes. Then, the discs were placed on filter paper for eliminating the excess bacteria and incubated in a co-culture medium for 48 hours (Trinca, S.; De Pace C.; Caccia, R.; Mugnozza, G. S.; Dodds, J. H. Jaynes, J. Transformation of potato (*Solanum tuberosum* L.) leaf disc using *A. tumefaciens* transfer DNA sequences coding for lytic peptides. Molecular methods for potato improvement. Lima: CIP, 1991. 85p). After co-culture, the explants were transferred to a selection medium (co-culture medium supplemented with kanamycin 50 mg/L and cephotaxim 50 mg/L). The transformation efficiency of the explants was evaluated by the transient and stable expression of the GUS gene in the tissues of the regenerated propagules.

Example 12—Analysis of GUS Expression

Figure 7:
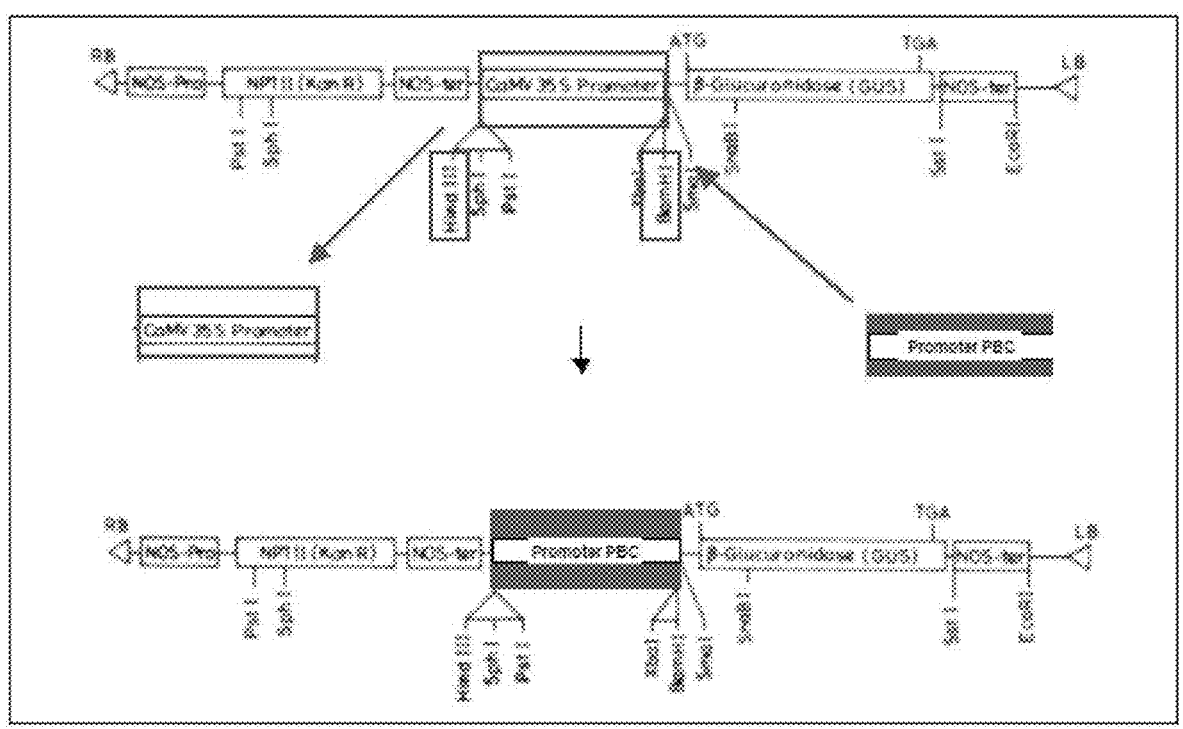
FIG. 7—reconstruction of the binary vector PBI121; the vector PBI121 has 12800 pb in length and its access number at the Gen Bank is AF485783; the construct of interest has been obtained by replacing the promoter CaMV 35S (835 pb) by the fragment of 451 pb of promoter CaLTP1.
Figure 8:
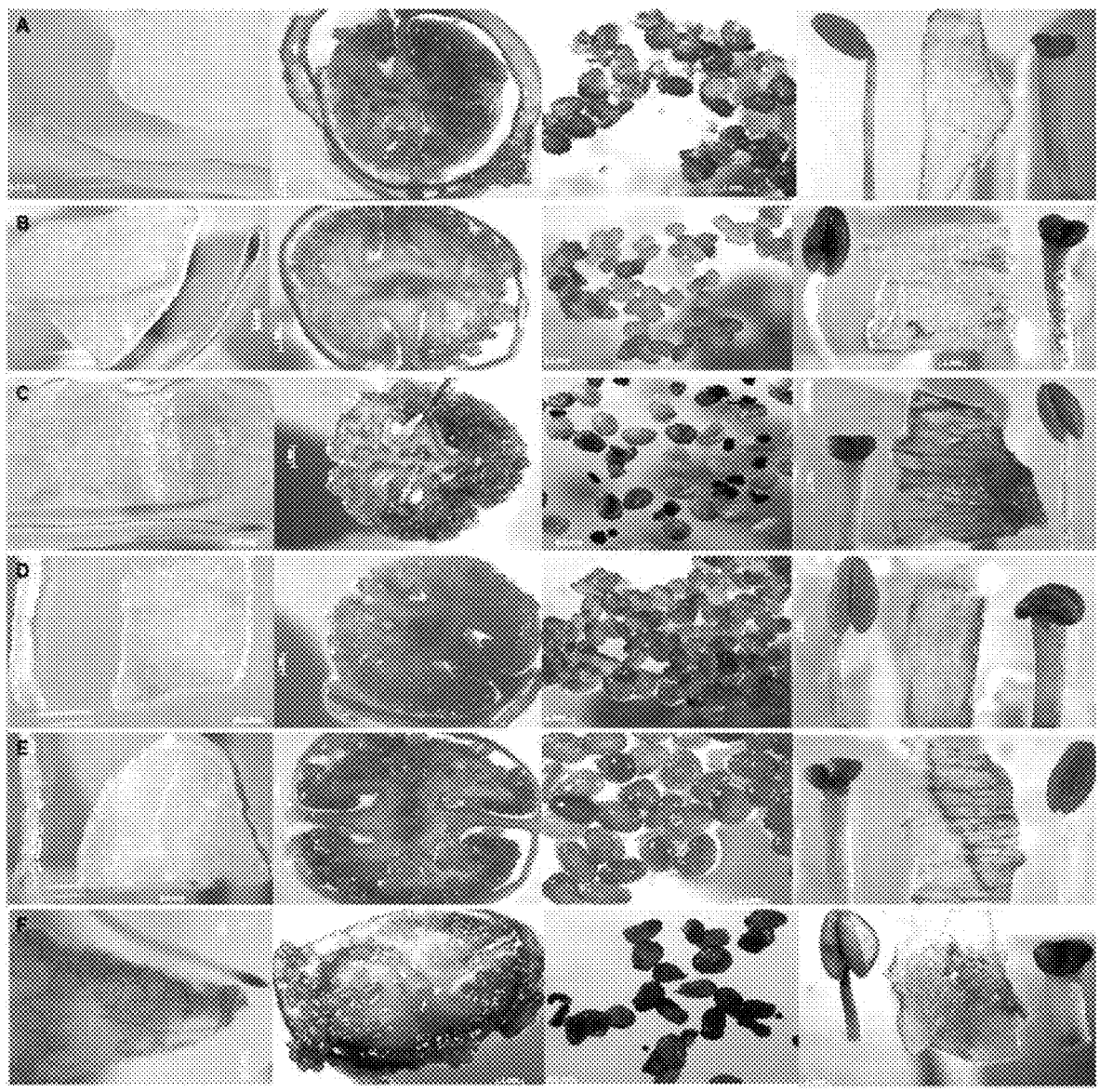
FIG. 8—location of the activity of GUS in tobacco plants transformed with the fragment of 451 pb of promoter CaLTP1. A, B, C, D; e I, J, K, L represent the negative and positive controls (PBI 121) of the experiment, respectively; A, E and I represent foliar and radicular tissues; B, F and J cross sections of fruits; C, G and K seeds; D, H and L stamen, petal and gynoecium. E, F, G and H represent the activity of the promoter CaLTP1; one can observe the reaction diagnose only in the seeds (G) of plants that contain the endosperm-specific promoter.

The promoter fragment of 451 base pairs is capable of commanding the expression of the reporter gene gus of tobacco plants (FIG. 7). The analysis of the expression of gus was made by histochemical assay according to adaptation of the protocol described by Jefferson (Jefferson R. A., Kavangh T. A. and Bevan M. W. 1987. GUS fusions: β-glucuronidase as a sensitive and versatile gene fusion marker in higher plants. EMBO J. 6: 3901-3907) in leaves, roots, fruits, seeds and flowers (petals, gynaeceum, stamen, pollen) of plants transformed with the promoter of 451 pb and the positive and negative controls. The cuts were made by hand with the aid of a scalpel, and the samples were dipped into the reaction buffer consisting of: 1 mM X-gluc (5-bromo-4-chloro-3-indolyl-β-D-glucuronide cyclohexylammonium salt), 10 mM of EDTA, 0.5 mM of potassium ferricyanide, and 0.5 mM of potassium ferricyanide, Triton X-100 0.1%, in 100 mM of $NaH_2PO_4$. $H_2O$. One adjusted the pH of the solution to 7.0 with NaOH and filtered in grow growth chamber. After the 5-minute pass of vacuum infiltration (5 mmHg), the samples were incubated at 37° C. overnight.

The invention claimed is:

1. A nucleic acid molecule, wherein said nucleic acid molecule comprises a polynucleotide sequence having promoter activity which has at least 95% sequence identity to the nucleotide sequence of SEQ ID NO: 1, wherein the polynucleotide sequence is linked to a nucleotide sequence that is heterologous with respect to SEQ ID NO: 1.

2. The nucleic acid molecule according to claim 1, wherein said nucleic acid molecule further comprises one or more expression-enhancing sequences.

3. The nucleic acid molecule according to claim 1, wherein said nucleotide sequence heterologous to SEQ ID NO: 1 comprises a coding region encoding a protein of interest.

4. The nucleic acid molecule according to claim 3, wherein the nucleotide sequence that is heterologous with respect to SEQ ID NO: 1 is in the sense orientation.

5. The nucleic acid molecule according to claim 2, wherein the one or more expression-enhancing sequences are from a virus selected from the group consisting of Simian Virus 40 (SV40), Herpes Simplex Virus type 1 (HSV-1), Alfalfa Mosaic Virus (AMV), and Human Papillomavirus 16 (HPV-16).

6. A recombinant vector comprising the nucleic acid molecule according to claim 1.

7. The recombinant vector according to claim 6, wherein said recombinant vector further comprises one or more expression-enhancing sequences and a termination sequence.

8. The recombinant vector according to claim 7, wherein the nucleotide sequence heterologous to SEQ ID NO: 1 comprises a coding region encoding a protein of interest.

9. The recombinant vector according to claim 7, wherein said vector comprises a termination sequence selected from the group consisting of termination signal of SV40, the adenylation signal of Herpes Simplex Virus thymidine kinase (HSV TK), termination signal of the gene of nopaline synthase of *Agrobacterium tumefasciens* (NOS), termination signal of the gene 19S and 35S of Cauliflower mosaic virus (CaMV), termination signal of the maize alcohol dehydrogenase, termination signal of the gene of manopine synthase, termination signal of the gene of beta-phaseoline, termination signal of the gene of small subunit of ribulose-1,5-bisphosphate carboxylase/oxygenase (ssRUBISCO), termination signal of the gene of sucrose synthase, termination signal of Subterranean clover stunt virus (SCSV), and termination signal of the gene trpC of *Aspergillus nidulans*.

10. The recombinant vector according to claim 7, wherein the one or more expression enhancing sequences are from a virus selected from the group consisting of SV40, HSV-1, Alfalfa Mosaic Virus (AMV), and HPV-16.

11. A transformed cell, wherein said transformed cell comprises the recombinant vector according to claim 6.

12. A plant, or a part, or a propagule, or progeny thereof, which comprises the recombinant vector according to claim 6.

13. A method for expressing a protein of interest in a plant, said method comprising stably incorporating into the genome of the plant the recombinant vector according to claim 8.

14. A method for producing a plant expressing a protein of interest, said method comprising:
   a) transforming at least one plant cell with the recombinant vector according to claim 8;

b) selecting a cell transformed with said recombinant vector in step (a); and
c) producing a mature plant from the transformed cell selected in step (b).

15. A method for expressing a protein of interest in a plant, said method comprising stably incorporating into the genome of the plant the nucleic acid molecule according to claim 3.

16. A method for producing a plant expressing a protein of interest, said method comprising:
   a) transforming at least one plant cell with the nucleic acid molecule according to claim 3;
   b) selecting a cell transformed with said nucleic acid molecule in step (a); and
   c) producing a mature plant from the transformed cell selected in step (b).

* * * * *

SEQUENCE LISTING

<160> NUMBER OF SEQ ID NOS: 10

<210> SEQ ID NO 1
<211> LENGTH: 484
<212> TYPE: DNA
<213> ORGANISM: Coffea arabica

<400> SEQUENCE: 1

```
ctcccacttc tcaaaacttg gataacgtcc gttgctgatt caatcatgag gattaattag      60
cttctggctt tttttgtgtt tctgggaaat tttgcttaaa gattaacttc cacttctcaa     120
aacttggata acgtccgttg ctgattcact catgaggatt aattagcttc tggctttttg     180
tgtttcggga cgtttttttct tttgttttt cccggtgatt tgttggaaag caattactct     240
gctttgtatc tttctcattt ttggccgaac aagtgaatgg gacactacgc gttattggcc     300
ctcttattca ctgattcatg agatcctcga gagccaatgc ccgctatcta caactataaa     360
tgcactaatt agcagagcaa aattttcagg aaacagtcga acggatctac agaatttcat     420
ttaactttct cttctgcact ttttgctttt cataatgatg aagaaatcat ctggggttgc     480
actg                                                                   484
```

<210> SEQ ID NO 2
<211> LENGTH: 29
<212> TYPE: DNA
<213> ORGANISM: Coffea arabica

<400> SEQUENCE: 2

```
acgactagtg aaatcatctg gggttgcac                                         29
```

<210> SEQ ID NO 3
<211> LENGTH: 36
<212> TYPE: DNA
<213> ORGANISM: Coffea arabica

<400> SEQUENCE: 3

```
gactactagc ggccgcttct cgttcaacac cattac                                 36
```

<210> SEQ ID NO 4
<211> LENGTH: 20
<212> TYPE: DNA
<213> ORGANISM: Coffea arabica

<400> SEQUENCE: 4

```
gaaatcatct ggggttgcac                                                   20
```

<210> SEQ ID NO 5
<211> LENGTH: 20
<212> TYPE: DNA
<213> ORGANISM: Coffea arabica

<400> SEQUENCE: 5

```
aagcatggac tcaatgcttg                                                   20
```

<210> SEQ ID NO 6
<211> LENGTH: 22
<212> TYPE: DNA
<213> ORGANISM: Coffea arabica

<400> SEQUENCE: 6

```
gtaatacgac tcactatagg gc                                                22
```

```
<210> SEQ ID NO 7
<211> LENGTH: 25
<212> TYPE: DNA
<213> ORGANISM: Coffea arabica

<400> SEQUENCE: 7
cagatccacc agcaacagta caacc                                              25

<210> SEQ ID NO 8
<211> LENGTH: 19
<212> TYPE: DNA
<213> ORGANISM: Coffea arabica

<400> SEQUENCE: 8
actatagggc acgcgtggt                                                     19

<210> SEQ ID NO 9
<211> LENGTH: 25
<212> TYPE: DNA
<213> ORGANISM: Coffea arabica

<400> SEQUENCE: 9
cagtgcaacc ccagatgatt tcttc                                              25

<210> SEQ ID NO 10
<211> LENGTH: 10
<212> TYPE: DNA
<213> ORGANISM: Coffea arabica

<400> SEQUENCE: 10
gccacctcat                                                               10
```